(12) United States Patent
Lu

(10) Patent No.: US 6,669,666 B2
(45) Date of Patent: Dec. 30, 2003

(54) SAFETY SYRINGE

(76) Inventor: Wen-Chin Lu, 12F, No. 333, Chung-Hsiao E. Road, Sec. 4, Taipei (TW)

(*) Notice: Subject to any disclaimer, the term of this patent is extended or adjusted under 35 U.S.C. 154(b) by 114 days.

(21) Appl. No.: 09/953,460

(22) Filed: Sep. 6, 2001

(65) Prior Publication Data

US 2003/0060778 A1 Mar. 27, 2003

(51) Int. Cl.[7] .................................................. A61M 5/32
(52) U.S. Cl. ........................................ 604/110; 604/195
(58) Field of Search ................................ 604/110, 195, 604/187, 192, 198, 263

(56) References Cited

U.S. PATENT DOCUMENTS 5,533,975 A * 7/1996 Lu .............................. 604/110

* cited by examiner

Primary Examiner—Brian L. Casler
Assistant Examiner—Kevin C. Sirmons

(57) ABSTRACT

A safety syringe includes: a syringe cylinder having a plurality of sleeve ribs formed in a sleeve portion of the syringe cylinder, a needle device having a needle detachably coupled on an shank portion which is provided with a plurality of shank ribs on the shank portion to be engaged with the sleeve ribs in the sleeve portion, with the needle device retractable in and automatically biased in the syringe cylinder to prevent outward protruding of used needle; whereby upon external connecting and rotative coupling of the needle on the shank portion, the shank portion will be locked without being rotatable, thereby enhancing a smooth coupling of the needle on the shank portion of the needle device.

3 Claims, 3 Drawing Sheets

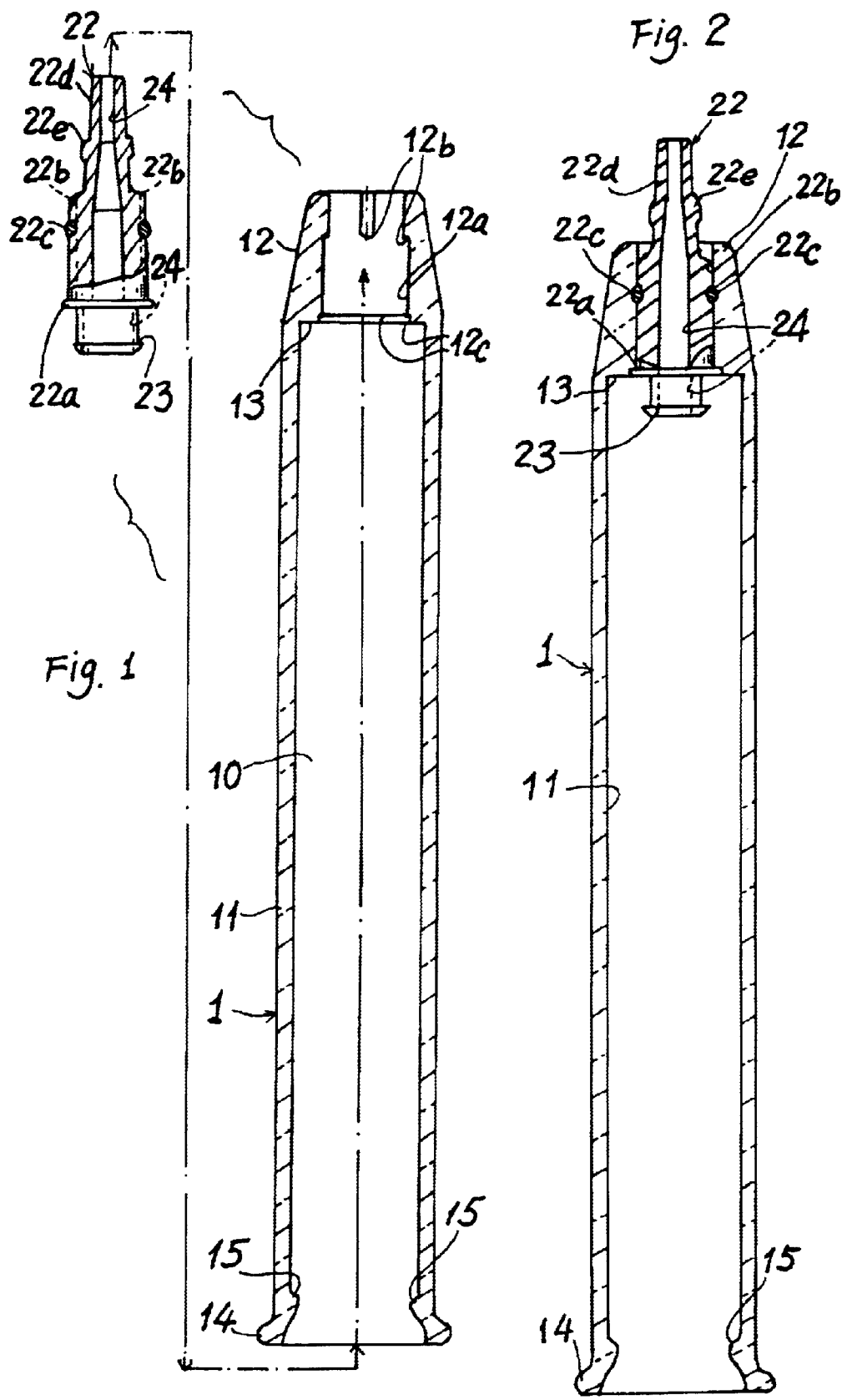

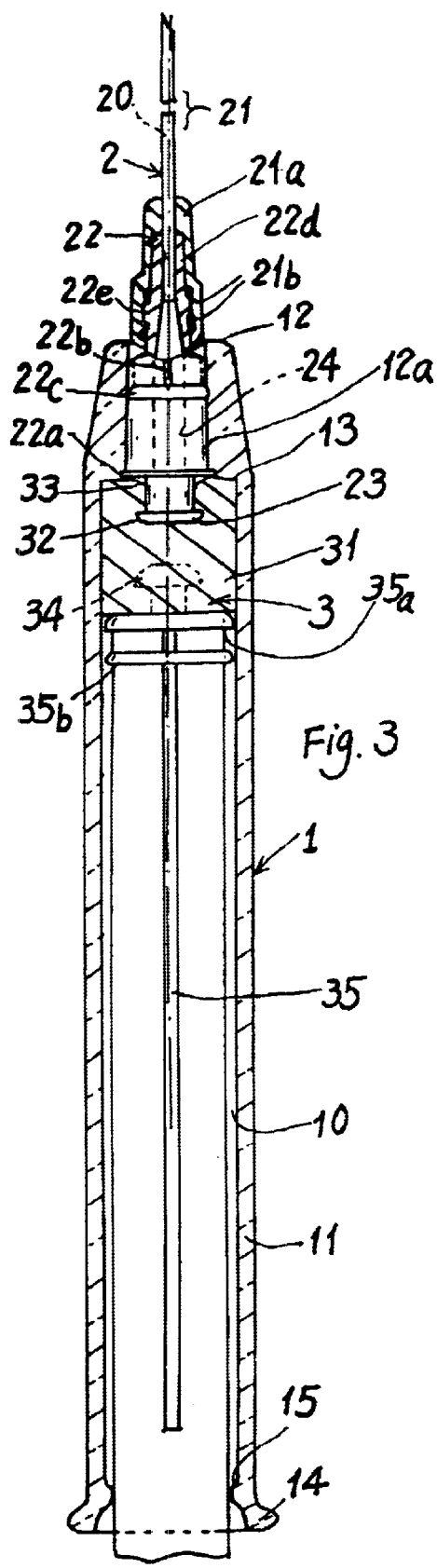
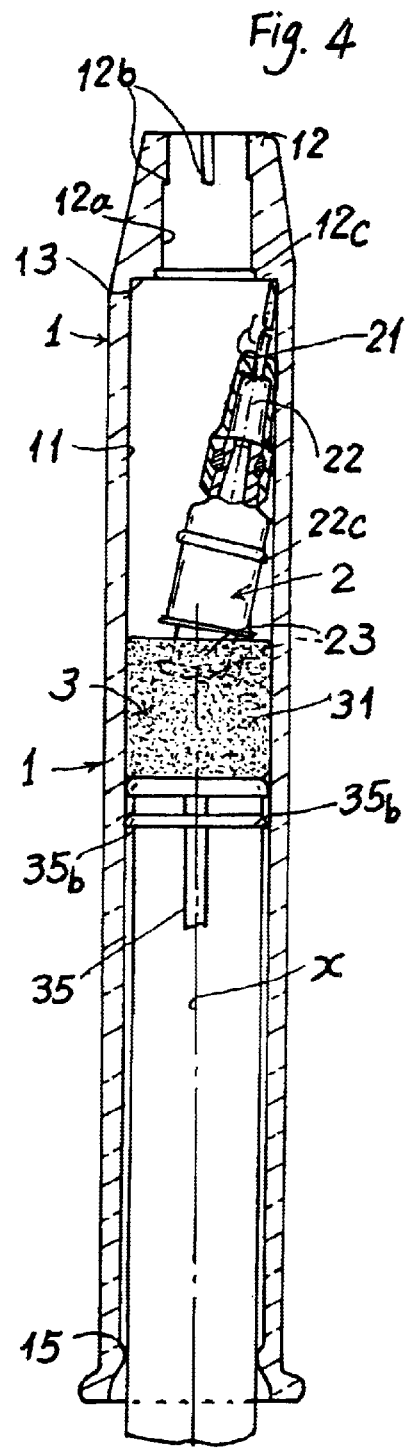

SAFETY SYRINGE

BACKGROUND OF THE INVENTION

This invention is an improvement of U.S. Pat. No. 5,533,975 (hereinafter called "prior art") also invented by the present inventor.

The prior art disclosed a safety syringe for automatically tilting a used needle when retracted into the syringe to prevent re-protrusion of the needle outwardly. A cylindrical recess 125 is recessed in the front portion of the syringe 1 provided with two wedged extensions 126 formed on the recess 125 for retarding two bars 225 diametrically formed on a cylindrical portion 224 of the shank portion 22 of the needle assembly, thereby preventing rotation of the shank portion when rotatably coupling the needle portion 21 and the shank portion 22. However, such a cylindrical recess 125 will be accumulated with liquid medicine to form a "dead pool" which can not be completely injected into a patient, causing waste of the medicine.

The present inventor has found the drawbacks of the prior art and invented the present improved safety syringe.

SUMMARY OF THE INVENTION

The object of the present invention is to provide a safety syringe including: a syringe cylinder having a plurality of sleeve ribs formed in a sleeve portion of the syringe cylinder, a needle device having a needle detachably coupled on an shank portion which is provided with a plurality of shank ribs on the shank portion to be engaged with the sleeve ribs in the sleeve portion, with the needle device retractable in and automatically biased in the syringe cylinder to prevent outward protruding of used needle; whereby upon external connecting and rotative coupling of the needle on the shank portion, the shank portion will be locked without being rotatable, thereby enhancing a smooth coupling of the needle on the shank portion of the needle device.

Another object of the present invention is to provide a safety syringe including an annular extension annularly formed on an inside wall of the syringe cylinder adjacent to a rear end of the syringe cylinder and at least a ratchet tooth formed on a front portion of a plunger slidably held in the syringe cylinder; whereby the annular extension provides a stopper for preventing a rearward releasing of the plunger from the cylinder since the ratchet tooth on the plunger will be locked against the annular extension when accidentally pulling the plunger rearwardly outwardly.

BRIEF DESCRIPTION OF THE DRAWINGS

FIG. 1 is a sectional drawing showing a shank portion of a needle device separated from a syringe cylinder of the present invention.

FIG. 2 is a sectional drawing of the present invention when assembled from FIG. 1.

FIG. 3 is a sectional drawing showing the engagement of the needle device with the plunger when finishing an injection in accordance with the present invention.

FIG. 4 shows a retracted and tilted needle in a syringe cylinder of the present invention.

DETAILED DESCRIPTION

Figure 5:
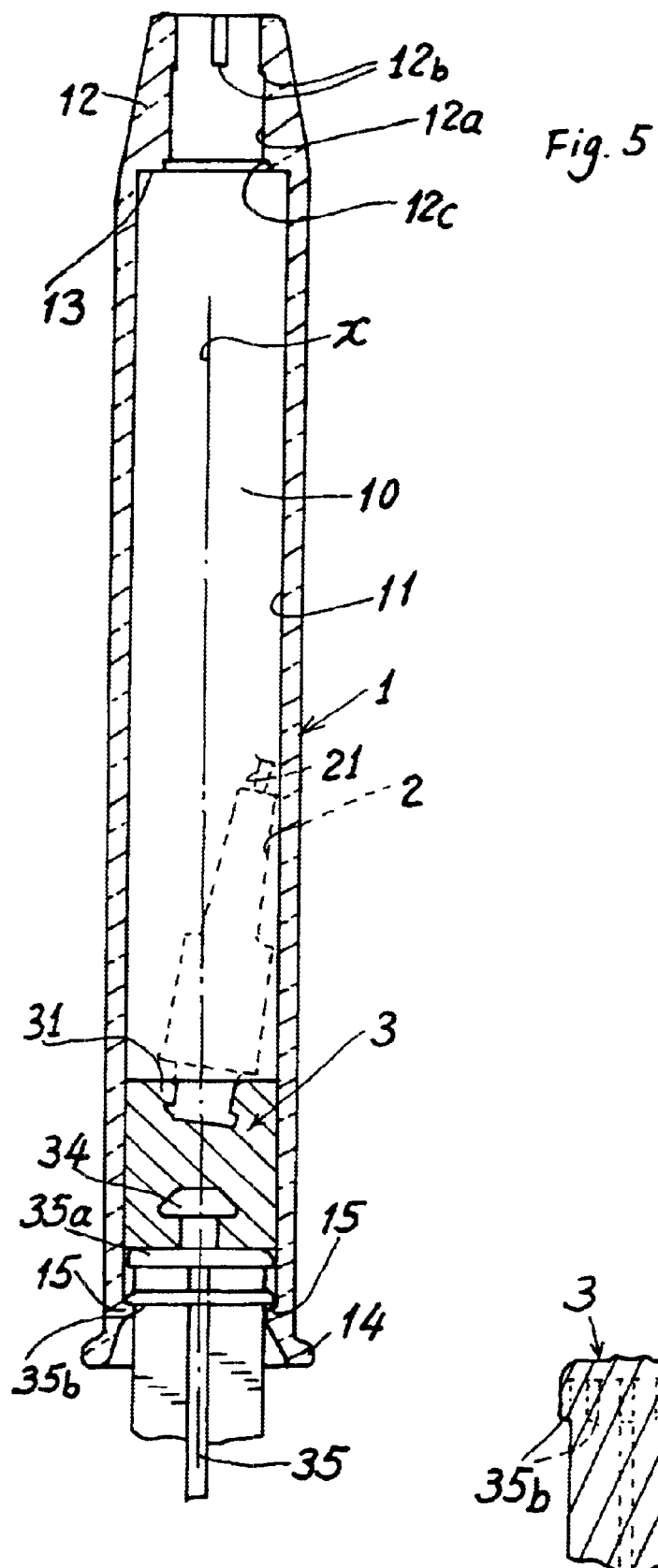
FIG. 5 is an illustration showing the prevention of an outward releasing of the plunger from the syringe cylinder.

As shown in FIGS. 1~5, the safety syringe of the present invention comprises: a syringe means 1; a needle device 2 detachably secured on the syringe means 1; and a plunger means 3 slidably held in the syringe means 1.

The syringe means 1 includes: a syringe cylinder 11 having an interior 10 for filling liquid medicine therein, a sleeve portion 12 formed on a front portion of the cylinder 11 having a sleeve hole 12a formed through the sleeve portion 12, a shoulder portion 13 formed in between the sleeve portion 12 and the cylinder 11, a syringe handle 14 formed on a rear end of the cylinder 11, and an annular extension 15 annularly formed on an inside wall of the cylinder 11 adjacent to the syringe handle 14.

The sleeve portion 12 has a plurality of sleeve ribs 12b longitudinally formed on an inside wall of the sleeve hole 12a, and a shallow recess 12c recessed in a rear portion of the sleeve portion 12 and having a diameter of the shallow recess 12c slightly larger than the diameter of the sleeve hole 12a (FIG. 4).

The needle device 2 includes: a hollow needle 21 having a needle hole 20 formed through the needle 21 and having a coupling sheath 21a secured to a rear portion of the needle 21 and formed with female threads 21b in the coupling sheath 21a; a shank portion 22 detachably secured in the sleeve hole 12a of the sleeve portion 12 to be coupled with the coupling sheath 21a of the needle 21; and a locking head portion 23 formed on a rear end of the shank portion 22 having a discharge slot 24 formed in the locking head portion 23 and in the shank portion 22 to be fluidically communicated with the needle hole 20 of the hollow needle 21 for passing the liquid medicine through the relevant holes 24, 20 to be injected into a patient's body.

The shank portion 22 includes: a shallow disk portion 22a formed on a rear end of the shank portion 22 to be engaged with the shallow recess 12c when securing the shank portion 22 in the sleeve portion 12, a plurality of shank ribs 22b longitudinally formed on a circumference of the shank portion to be engaged with the sleeve ribs 12b in the sleeve portion 12, a packing ring 22c disposed about the shank portion 22 and engaged with the inside wall of the sleeve hole 12a and forwardly retarded by the rib ends of the sleeve ribs 12b when mounting the shank portion 12 in the sleeve portion 12 for preventing leakage during injection of the needle 21, and a stem portion 22d formed on a front portion of the shank portion 22 having a pair of projections 22e circumferentially formed on the stem portion 22d for engaging the female threads 21b formed in the coupling sheath 21a of the needle 21 for externally connecting the coupling sheath 21a of the needle with the shank portion 22 previously secured in the sleeve portion 12 of the syringe cylinder 11.

The plunger means 3 includes: a plunger 31 secured on a front end portion 34 of a plunger rod 35 slidably held in the syringe cylinder 11, a biasing socket 32 recessed in the plunger 31 for engaging the locking head portion 23 of the needle device 2 through a guiding port 33 formed in the plunger 31 after finishing the injection, and at least a ratchet tooth 35b formed on a rear portion of a circular disk 35a (having arcuate front edge portion on the disk 35a) formed on a front portion of the plunger rod 35, with the ratchet tooth 35b operatively retarded against the annular extension 15 formed in the cylinder 11 when pulling the plunger rod 35 rearwardly outwardly (FIG. 5) for preventing a rearward releasing of the plunger means 3 from the cylinder 11 after finishing the injection.

When assembling the hollow needle 21 of the present invention, the coupling sheath 21a of the needle 21 is rotated to engage the female threads 21b therein with the projections 22e on the stem portion 22d, the shank ribs 22b will be engaged and retarded by the sleeve ribs 12b in the sleeve portion 12 to prevent from a rotation of the shank portion 22, thereby allowing a smooth rotation of the coupling sheath 21a about the shank portion 22 until firmly securing the sheath 21a (of the needle 21) on the shank portion 22 which is already secured in the sleeve portion 12 of the syringe means 1.

The cylindrical recess 125 and the extensions 126 as provided in the front portion of the syringe of the prior art are now eliminated, indicating that there is no "dead pool" formed in the front portion of the syringe cylinder of the present invention and thereby exhausting all liquid medicine in the cylinder after completing the injection without wasting the liquid medicine and being superior to the prior art.

After completing the injection, the locking head portion 23 of the needle device 2 as engaged with the biasing socket 32 in the plunger will be simultaneously retracted into the cylinder 11 and will be automatically tilted from the axis X (from FIG. 3 to FIG. 4) for a safe protection of the syringe.

Figure 6:
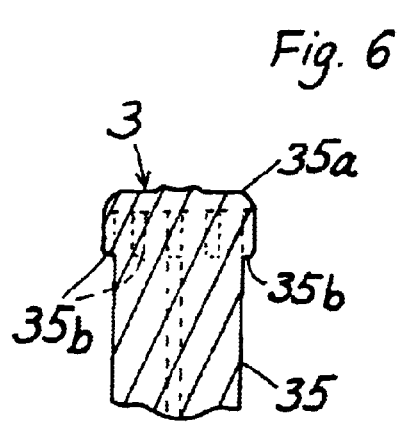
FIG. 6 shows another embodiment of the plunger means having ratchet tooth formed thereon.

The ratchet tooth (or teeth) 35b as recessed or formed in a rear portion of the circular disk 35a of the plunger means 3 can be plural ratchet teeth 35b (the number and shapes of teeth being not limited) circumferentially formed in a front portion of the plunger rod 35 as shown in FIG. 6 or may be formed as an annular ratchet tooth 35b annularly formed on a front portion of the plunger rod 35 as shown in FIG. 5.

The arcuate front edge portion of the circular disk 35a on the front end portion of the plunger rod 35 may be smoothly inserted into the interior 10 of the syringe cylinder 11 by passing through the annular extension 15 when assembling the plunger means 3 in the cylinder 11. However, when rearwardly pulling the plunger rod 35 as shown in FIG. 5, the ratchet tooth (or teeth) 35b will be retarded or locked on the annular extension 15 to thereby prevent from an outward rearward releasing of the plunger means 3 from the cylinder 11, especially when coupled with a tilted needle 21 thereon (FIGS. 4 & 5).

Accordingly, the present invention really provides a safety syringe to prevent from a forward protruding of a used needle as retracted in the syringe cylinder (FIG. 4); and also to prevent from a rearward releasing of the plunger 31 coupled with the used needle 21 from the cylinder 11 (FIG. 5). The used needle 21 will be well "trapped" in the cylinder 11 for absolutely ensuring the safety protection of a syringe (for preventing from sticking injury of a used needle to a nurse, a doctor, a hospital cleaner or housekeeper, etc.)

The present invention may be modified without departing from the spirit and scope of the present invention.

The present invention may be used for hypodermic injection and may also be modified to be used for intravenous injection.

I claim:

1. A safety syringe comprising:
    a syringe means having a syringe cylinder formed with a sleeve portion on a front portion of said syringe cylinder;
    a needle device detachably secured on said syringe cylinder and including: a hollow needle, a shank portion for externally connecting the hollow needle thereon and a locking head portion formed on a rear portion of said shank portion; and
    a plunger means slidably held in said syringe cylinder, having a plunger secured to a plunger rod and recessed with a biasing socket in said plunger for coupling said locking head portion of said needle device in said biasing socket when completing an injection, said plunger as coupled with said needle device operatively retracted into said syringe cylinder for tilting said needle without re-protruding said needle forwardly from said sleeve portion;
    the improvement which comprises:
        said sleeve portion having a plurality of sleeve ribs longitudinally formed on an inside wall in a sleeve hole formed through said sleeve portion;
        said shank portion having a plurality of shank ribs longitudinally formed on an outer surface of said shank portion for respectively engaging said sleeve ribs in said sleeve portion, and a shallow disk portion formed on a rear portion of said shank portion to be engaged with a shallow recess formed in a rear portion of said sleeve hole of said sleeve portion, whereby upon securing of said shank portion in said sleeve portion and upon rotation of said shank portion, said shank ribs on said shank portion will be engaged and locked by said sleeve ribs in said sleeve portion for preventing a rotation of said shank portion, thereby allowing a smooth connection of said hollow needle on said shank portion on said syringe cylinder; and
    said plunger means including at least a ratchet tooth formed on a rear portion of a circular disk which is formed on a front end portion of said plunger rod adjacent to said plunger, and said syringe cylinder having an annular extension annularly formed in a rear portion of said syringe cylinder; whereby upon a rearward pulling of said plunger rod, said ratchet tooth will be engaged and locked by said annular extension in said syringe cylinder for preventing a rearward releasing of said plunger means from said syringe cylinder once inserted into said syringe cylinder.

2. A safety syringe according to claim 1, wherein said shank portion further includes a packing ring annularly formed on said shank portion to be engaged with an inside wall of said sleeve hole in said sleeve portion, and said packing ring forwardly limited by said sleeve ribs in said sleeve portion.

3. A safety syringe according to claim 1, wherein said ratchet tooth is formed as an annular ratchet tooth annularly formed in a rear portion of said circular disk as formed on a front end portion of said plunger rod.

* * * * *